United States Patent [19]
Bao et al.

[11] Patent Number: 5,192,326
[45] Date of Patent: Mar. 9, 1993

[54] HYDROGEL BEAD INTERVERTEBRAL DISC NUCLEUS

[75] Inventors: Qi-Bin Bao, Livingston; Paul A. Higham, Ringwood, both of N.J.

[73] Assignee: Pfizer Hospital Products Group, Inc., New York, N.Y.

[21] Appl. No.: 756,957

[22] Filed: Sep. 9, 1991

Related U.S. Application Data

[63] Continuation-in-part of Ser. No. 633,711, Dec. 21, 1990, Pat. No. 5,047,055.

[51] Int. Cl.⁵ ............................................. A61F 2/44
[52] U.S. Cl. ...................................... 623/17; 623/11; 623/16
[58] Field of Search ................. 623/16, 17, 18, 11; 606/60, 61

[56] References Cited

U.S. PATENT DOCUMENTS

| | | | |
|---|---|---|---|
| 3,867,728 | 2/1975 | Stubstad et al. | 623/17 |
| 3,875,595 | 4/1975 | Froning | 623/17 |
| 4,772,287 | 9/1988 | Ray et al. | 623/17 |
| 4,904,260 | 2/1990 | Ray et al. | 623/17 |
| 4,911,718 | 3/1990 | Lee et al. | 623/18 |

FOREIGN PATENT DOCUMENTS 2639823 6/1990 France ........................ 623/17

*Primary Examiner*—Ronald Frinks
*Attorney, Agent, or Firm*—Peter C. Richardson; Lawrence C. Akers; Raymond W. Augustin

[57] ABSTRACT

A prosthetic nucleus for implantation in the disc space after removal of a damaged or degenerated nucleus is formed from a multiplicity of hydrogel beads having a water content of at least 30%. The beads are covered by a semi-permeable membrane. The membrane has porosity less than the size of the beads to thereby retain the beads therein but permit fluids to flow in and out of the prosthetic nucleus.

26 Claims, 8 Drawing Sheets

HYDROGEL BEAD INTERVERTEBRAL DISC NUCLEUS

BACKGROUND OF THE INVENTION

This application is a continuation-in-part of co-pending application Ser. No. 07/633,711 filed Dec. 21, 1990, now U.S. Pat. No. 5,047,055.

FIELD OF THE INVENTION

This invention relates to a prosthetic intervertebral disc nucleus. More particularly it relates to an artificial disc nucleus made of a hydrogel material. The hydrogel material may be either in bulk or beaded form.

The intervertebral disc is a complex joint anatomically and functionally. It is composed of three component structures: the nucleus pulposus, the annulus fibrosus and the vetebral end-plates. The biomedical composition and anatomical arrangements within these component structures are related to the biomechanical function of the disc.

The nucleus pulposus occupies 25-40% of the total disc cross-sectional area. It is composed mainly of mucoid material containing mainly proteoglycans with a small amount of collagen. The proteoglycans consist of a protein core with chains of negatively charged keratin sulphate and chondroitin sulphate attached thereto. Due to these constituents, the nucleus pulposus is a "loose or amorphous hydrogel" which has the capacity to bind water and usually contains 70-90% water by weight. Although the nucleus plays an important role in the biomechanical function of the disc, the mechanical properties of the disc are not well known, largely because of the loose hydrogel nature of the nucleus.

Because the nucleus is surrounded by the annulus fibrosus and vertebral endplates, and the negatively charged sulphate groups are immobilized due to the attachment of these groups to the polymer matrix, this causes the matrix to have a higher concentration of ions than its surroundings. This higher concentration results in a higher osmotic pressure ranging between 0.1-0.3 MPa. As a result, the high fixed charge density of the proteoglycan leads the matrix to exert an osmotic swelling pressure which can support an applied load in much the same way as air pressure in a tire supports the weight of a car.

It is the osmotic swelling pressure and hydrophilicity of the nucleus matrix that offers the nucleus the capability of imbibing fluid until it is balanced with the resistance stresses coming internally from the tensile forces of the collagen network and externally from the loads that are applied by muscle and ligament tension. The swelling pressure (Ps) of the nucleus is dependent on the concentration of proteoglycan, i.e. the higher proteoglycan concentration, the higher swelling pressure of the nucleus, and vise versa. This external pressure changes with posture. When the human body is supine, the compressure load on the third lumbar disc is 300 newtons (N), which rises to 700N when upright stance is assumed and to 1200N when bending forward by only 20°. When the external pressure (Pa) increases, it breaks the previous balance of Ps=Pa. To reach the new balance, the swelling pressure (Ps) has to increase. This increase is achieved by increasing the proteoglycan concentration in the nucleus which is in turn achieved by reducing the fluid in the nucleus. That is why discs will lose about 10% of their height as a result of creep during the daytime. When the external load is released (Ps>Pa), the nucleus will imbibe fluid from its surroundings in order to reach the new equilibrium. It is this property of the nucleus that is mainly responsible for the compressive properties of the disc.

The annulus fibrosus forms the outer limiting boundary of the disc. It is composed of highly structured collagen fibers embedded in amorphous base substance also composed of water and proteoglycans, which is lower in content in the annulus than in the nucleus. The collagen fibers of the annulus are arranged in concentric laminated bands (8-12 layers thick) with a thicker anterior wall and thinner posterior wall. In each lamella, the fibers are parallel and attached to the superior and inferior vertebral bodies at roughly a 30° angle from the horizontal plane of the disc in both directions. This design particularly resists twisting, as half of the angulated fibers will tighten as the vertebrae rotate relative to each other in either direction.

The composition of the annulus fibrosus along the radial axis is not uniform. There is a steady increase in the proportion of collagen from the inner to the outer annulus. This difference in composition may reflect the need of the inner and outer regions of the annulus to blend into very different tissues while maintaining the strength of the structure. Only the inner lamellae are anchored to the end-plates forming an enclosed vessel for the nucleus. The collagen network of the annulus restrains the tendency of the nucleus gel to absorb water from surrounding tissues and swell. Thus, the collagen fibers in the annulus are always in tension, and the nucleus gel is always in compression.

The two vertebral end-plates are composed of hyaline cartilage, which is a clear "glassy" tissue, and separates the disc from the adjacent vertebral bodies. This layer acts as a transitional zone between the hard, bony vertebral bodies and the soft disc. Because the intervertebral disc is avascular, most nutrients that the disc needs for metabolism are transported to the disc by diffusion through the end-plate area.

The intervertebral joint exhibits both elastic and viscous behavior. Hence, during the application of a load to the disc there will be an immediate "distortion" or "deformation" of the disc, often referred to as "instantaneous deformation". It has been reported that the major pathway by which water is lost from the disc during compression is through the cartilage end-plates. Because the permeability of the end-plates is in the range $(0.20-0.85) \times 10^{-17}$ $m^4N^{-1}$, it is reasonable to assume that under loading, the initial volume of the disc is constant while the load is applied. Because the natural nucleus of the disc is in the form of loose hydrogel which can be deformed easily, the extent of deformation of the disc is largely dependent on the extensibility of the annulus. It is generally believed that the hydrostatic behavior of the nucleus pulposus plays an important role in the normal static and dynamic load-sharing capability of the disc and the restoring force of stretched fibers of the annulus balances the effects of nucleus swelling pressure. Without the constraint from the annulus, nucleus annular bulging increases considerably. If the load is maintained at a constant level, a gradual change in joint height will occur as a function of time which is commonly referred to as "creep". Eventually, the creep will stabilize and the joint is said to be in "equilibrium". When the load is removed the joint will gradually "recover" to its original height before loading (the creep and relax rate depends on the amount of load applied, the permeability of the end-plates and the water binding capability of the nucleus hydrogel). The creep and relax is an essential process to pumping the fluid in and out of the disc.

Degeneration of the intervertebral disc is believed to be a common cause of final pathology and of back pain. As the intervertebral disc ages, it undergoes degeneration. The changes that occur are such that in many respects the composition of the nucleus seems to approach that of the inner annulus fibrosus. Intervertebral disc degeneration is, at least in part, the consequence of the composition change of the nucleus. It has been found that both the molecular weight and the content of proteoglycans from the nucleus decreases with age, especially in degenerated discs, and the ratio of keratin sulphate to chondroitin sulphate in the nucleus increases. This increase in the ratio of keratin sulphate to chondroitin sulphates and decrease in proteoglycan content decreases the fixed charge density of the nucleus from 0.28 meq/ml to about 0.18-0.20 meq/ml. These changes cause the nucleus to lose its water binding capability and its swelling pressure. As a result, the nucleus becomes less hydrated, and its water content drops from over 85% in preadolescence to about 70-75% in middle age. The glycosaminoglycan content of prolapsed discs has been found to be lower, and the collagen content higher than that of normal discs of a comparable age. Discs L-4-L-5 and L-5-S-1 are usually the most degenerated discs.

It is known that although the nucleus only has about one third of the total disc area, it takes about 70% of the total loading in a normal disc. It has been found that the load in the nucleus of moderately degenerated discs is 30% lower than in comparable normal discs. However, the vertical load on the annulus fibrosus increases by 100% in the degenerated discs. This load change is primarily caused by the structural changes of the disc as discussed above. The excess load on the annulus of the degenerated discs would cause narrowing of the disc spaces and excessive movement of the entire spinal segments. The flexibility would produce excessive movement of the collagenous fibers that, in turn, would injure the fiber attachments and cause delamination of the well organized fibers of the annulus ring. The delaminated annulus can be further weakened by stress on the annulus and in severe cases this stress will cause tearing of the annulus. This whole process is very similar to driving on a flat tire, where the reinforcement layer will eventually delaminate. Because the thickness of the annulus is not uniform, with the posterior being thinner than the anterior, the delamination and the lesion usually occur in the posterior area first.

The spinal disc may also be displaced or damaged due to trauma or a disease process. In this case and in the case of disc degeneration, the nucleus pulposus may herniate and/or protrude into the vertebral canal or intervertebral foramen, in which case it is known as a herniated or "slipped" disc. This disc may in turn press upon the spinal nerve that exits the vertebral canal through the partially obstructed foramen, causing pain or paralysis in the area of its distribution. The most frequent site of occurrence of a herniated disc is in the lower lumbar region. A disc herniation in this area often involves the inferior extremities by compressing the sciatic nerve.

There are basically three types of treatment currently being used for treating low back pain caused by injured or degenerated discs: conservative care, laminectomy and fusion. Each of these treatments has its advantages and limitations. The vast majority of patients with low back pain, especially those with first time episodes of low back pain, will get better with conservative care treatment. However, it is not necessarily true that conservative care is the most efficient and economical way to solve the low back pain problem.

Laminectomy usually gives excellent short term results in relieving the clinical symptoms by removing the herniated disc material (usually the nucleus) which is causing the low back pain either by compressing the spinal nerve or by chemical irritation. Clearly a laminectomy is not desirable from a biomechanical point of view. In the healthy disc, the nucleus takes the most compressional load and in the degenerated disc this load has been distributed more onto the annulus ring, which, as described above, causes tearing and delamination. The removal of the nucleus in a laminectomy actually causes the compressive load to be distributed further on the annulus ring, which would narrow the disc spaces. It has been reported that a longterm disc height decrease might be expected to cause irreversible osteoarthritic-like changes in the adjacent facet joint. That is why laminectomy has poor long term results and high incidence of reherniation.

Fusion generally does a good job in eliminating symptoms and stabilizing the joint. However, because the motion of the fused segment is restricted, it increases the range of motion of the adjoining vertebral discs, possibly enhancing their degenerative processes.

Because of these disadvantages, it is desirable to develop a prosthetic joint device which not only is able to replace the injured or degenerated intervertebral disc, but also can mimic the physiological and the biomechanical function of the replaced disc. Such a device would restore the function of the disc and prevent further degeneration of the surrounding tissue.

DESCRIPTION OF THE PRIOR ART

Various artificial discs are well known. U.S. Pat. No. 3,867,728 to Stubstad et al, which issued on Feb. 25, 1975, relates to a device which replaces the entire disc. This device is made by laminating vertical, horizontal or axial sheets of elastic polymer. U.S. Pat. No. 3,875,595 to Froning, dated Apr. 8, 1975, relates to a collapsible plastic bladder-like prosthesis of nucleus pulposus. Another U.S. patent relates to a prosthesis utilizing metal springs and cups (Patil, U.S. Pat. No. 4,309,777). A spinal implant comprising a rigid solid body having a porous coating on part of the surface is shown in Kenna's U.S. Pat. No. 4,714,469. An intervertebral disc prosthesis of a pair of rigid plugs to replace the disc is shown in Kuntz, U.S. Pat. No. 4,349,921. Ray et al, U.S. Pat. Nos. 4,772,287 and 4,904,260, use a pair of cylindrical prosthetic intervertebral disc capsules with or without therapeutical agents. U.S. Pat. No. 4,904,260 also relates to the use of a semi-permeable membrane to cover the device. French Publication 2,639,823 relates to a nonpermeable polyethylene enclosure filled with polyurethane beads. U.S. Pat. No. 4,911,718 relates to an elastomeric disc spacer comprising three different parts; nucleus, annulus and end-plates, of different materials. At the present time, none of these concepts has become a product in the spinal care market.

The main reason for the difficulty in implementing these concepts is that except for the concepts of Froning's, Kuntz's and Ray's, these prostheses call for replacing the entire natural disc, which involves numerous surgical difficulties. Secondly, the intervertebral disc is a complex joint anatomically and functionally and it is composed of three component structures, each of which has its own unique structural characteristics. To design and fabricate such a complicated prosthesis from acceptable materials which will mimic the function of the natural disc is very difficult. A problem also exists in finding a way to prevent the prosthesis from dislodging. Thirdly, even for prostheses which are only intended for replacing the nucleus, a major obstacle is finding a material which is in character similar to the natural nucleus and also is able to restore the natural function of the nucleus. Neither silicone elastomers nor thermoplastic polymers are ideal for the prosthetic nucleus due to their significant inherent characteristic differences from the natural nucleus.

This problem is not solved by Kuntz, which involves using elastic rubber plugs, and Froning and Ray, which use bladders filled with a fluid or plastic or thixotropic gel. In both the latter cases, liquid was used to fill the bladder so that the bladder membrane had to be completely sealed to prevent fluid leakage. Clearly, the prior devices would not completely restore the function of the nucleus which allows the fluid to diffuse in and out during cyclic loading to allow body fluid diffusion which provides the nutrients the disc needs.

This invention relates to a new prosthetic lumbar disc nucleus which is made from synthetic hydrogels. Hydrogels have been used in biomedical applications in various areas such as contact lenses. Among the advantages of hydrogels are that they are more biocompatible than other hydrophobic elastomers and metals. This This biocompatibility is largely due to the unique characteristics of hydrogels in that they are soft and hydrated like the surrounding tissues and have relatively low friction with respect to the surrounding tissues. The biocompatibility of hydrogels results in a prosthetic nucleus more easily tolerated in the body.

An additional advantage is that some hydrogels have good mechanical strength which permits them to withstand the load on the disc and restore the normal space between the vertebral body. The prosthetic nucleus of the present invention has high mechanical strength and is able to withstand the body load and assist in the healing of the defective annulus.

Another advantage of the present invention is that many hydrogels have excellent visco-elastic properties and shape memory. Unlike other elastomeric polymers, hydrogels contain a large portion of water which acts as a plasticizer. Part of the water in the hydrogel is available as free water, which has more freedom to leave the hydrogel when the hydrogel is partially dehydrated or under mechanical pressure. This characteristic of the hydrogels enables them to creep in the same way as the natural nucleus under compression and to withstand cyclic loading for long periods without any significant degradation and without losing their elasticity. This is because water in the hydrogel behaves like a cushion which makes the network of the hydrogel less stretched.

In addition, hydrogels are permeable to water and water-soluble substances, such as nutrients, metabolites and the like. It is known that body fluid diffusions under cyclic loading is the major source of nutrients to the disc and if the route of this nutrient diffusion is blocked, it will cause further deterioration of the disc.

The hydrogels used in the disc of the present invention, as with many hydrogels, can be dehydrated and then hydrated again without changing the properties of the hydrogel. When the hydrogel is dehydrated, its volume will decrease, which makes it possible to implant the prosthetic nucleus in the dehydrated or unhydrated state. The implanted prosthetic nucleus will then swell slowly in the body. This feature makes it possible to implant the device posterior-laterally during an open surgery or even possibly percutaneously, thereby reducing the complexity and risk of intraspinal surgery traditionally used. The danger of perforation of the nerve, dural sac, arteries and other organs is reduced. The incision area on the annulus also can be reduced, thereby helping the healing of the annulus and preventing the reherniation of the disc. Hydrogels have also been used in drug delivery due to their capability for a controllable release of the drug. Different therapeutic agents, such as different growth factors, long term analgesics and anti-inflammatory agents can be attached to the prosthetic nucleus and be released in a controllable rate after implantation.

Furthermore, dimensional integrity is maintained with hydrogels having a water content of up to 99%. This dimensional integrity, if properly designed, distributes the load to a larger area on the annulus ring and prevents the prosthetic nucleus from bulging and herniating.

SUMMARY OF THE INVENTION

It is an object of the invention to provide a prosthetic nucleus for a disc which functions in a manner very similar to the natural nucleus.

It is yet another object of the invention to provide a prosthetic nucleus for a disc which is composed of a hydrogel material capable of balancing its hydrostatic pressure with external loads thereon.

These and other objects of the present invention are disclosed in a preferred embodiment of the invention which includes a prosthetic nucleus for a disc which is composed of a hydrogel material. The hydrogel material may be either in beaded or particle form or in bulk form (one or more large pieces) or in crosslinked gel form encapsulated in a flexible semi-permeable membrane. The hydrogel prosthetic nucleus as inflated has a shape and size generally conforming to the natural nucleus which has been removed in a regular discectomy procedure and has a water content of at least 30%, preferably 70–99%, with when in bulk form, a compressive strength of at least 4 Meganewton per square meter ($MNm^{-2}$) or greater when hydrated to its equilibrium water content. While the preferred bulk nucleus may have a water content of 70% to 85% when fully hydrated, it may have a water content of up to 90%. Each particle of the particulate prosthetic nucleus may have a water content of up to 99%.

The expansion factor of a dehydrated hydrogel will be dependent on the equilibrium water content (EWC) of that hydrogel. It may vary from 1.19 for a hydrogel of 38% EWC to 1.73 for a hydrogel of 80% EWC. Because the density of most organic polymers is close to 1, for an 90% EWC hydrogel, the volume of the dehydrated prosthetic nucleus is only about 10% of the hydrated one. For 99% EWC hydrogel, the dehydrated hydrogel would have a volume of 1 or 2% of the hydrated form. This volume change for the dehydrated or unhydrated hydrogel significantly reduces the size of the implant.

After hydration in the disc, the hydrogel nucleus will be constrained tightly in the cavity from which the nucleus has been excised. The constraining forces are the restoring force of the stretched fibers of the annulus and the external force through the end-plates. The constraint from the annulus and the end-plates will restrict the movement of the hydrogel nucleus and prevent it from bulging and herniating from the cavity.

The bulk prosthetic nucleus may be formed from two or more pieces of hydrogel material, each shaped so that when combined they have a shape generally conforming to the natural nucleus. Utilizing a two-piece bulk prosthetic nucleus facilitates implantation, which is done with the hydrogel material in a dehydrated or unhydrated state.

The present invention also relates to a new prosthetic lumbar disc nucleus which is made from synthetic hydrogel beads or particles sealed within a semi-permeable membrane.

An advantage of many hydrogels in beaded form is that they have excellent visco-elastic properties and shape memory.

In addition, hydrogels with higher water content can be used for the prosthetic nucleus because the hydrogel beads are contained in a mechanically strong membrane. Therefore, the requirements for mechanical strength and resistance to deformation under compressive or torsional load for the beaded hydrogel can be much less. Typically, as the water content of the hydrogel increases, the mechanical strength and resistance to deformation decrease. This will limit many high water content hydrogels from being used for a one-piece or two-piece bulk hydrogel prosthetic nucleus. Although it is known that the water content of the nucleus in the adult spinal disc is in the range of 70–80%, it has been found that the disc fragments will swell in saline solution up to 200–300% when unloaded in vitro (Hendry, N. G. C., Journal of Bone and Joint Surgery, 40B, 1958, pp. 132–144, and Hirsch, C. and Galante, J. Acta Orthopaedica Scandinavica, 38, 1967, pp. 148–162). This means that the actual water content of the natural nucleus under unloaded conditions is more than 90%. Therefore, it is more desirable to use a hydrogel with a water content of more than 90%.

Another advantage is that as the water content of the hydrogel increases, the visco-elasticity will also increase. The water in the hydrogel acts as a plasticizer, which makes the hydrogel beads more flexible and produce less debris from wear. A further advantage is that when the hydrogel material used is in the form of small beads or particulates, the beaded or particulated form of the hydrogel is better at withstanding impact and compressive or torsional load than the bulk hydrogel because the beaded form can dispense energy better.

When a beaded or even a bulk hydrogel is used and covered by a membrane, the hydrogel is not in direct contact with body tissue, a wider variety of hydrogels can be chosen, especially crosslinked polymers with charged groups, which have a very high water content. The water content of a hydrogel can normally be increased by introducing charged groups on the network of the polymer due to the increase in hydrophilicity of the polymer. For example, the Sephadex ® beads available from Pharmacia are made of a hydrogel prepared by crosslinking dextran with epichlorohydrin. The hydrophilicity of the neutral beads (G-types) is rendered by the large number of hydroxyl groups on the dextran polymer. The G-types of Sephadex differ in their crosslinking density and hence in their degree of swelling capability. As the charged groups are introduced into the network of the crosslinked polymer, e.g. carboxymethyl group attaching to the G-50 beads which, after crosslinking, are then named CM-C-50 beads by Pharmacia, the swelling capability increases from about 8 ml/g dry for Sephadex ® G-50 beads to 40 ml/g dry beads. However, the surface charge of these charged groups of attached to the hydrogels also enhance the interaction between the hydrogel and living cells or proteins. The adhesion of certain cells or absorption of certain proteins on the hydrogel may result in altering the mechanical properties of the hydrogel and in the worst case degrading the hydrogel polymer. These unwanted interactions can be avoided by using the membrane which will block the interactions between either bulk or particulate hydrogel and living cells or proteins.

With a membrane cover, the hydrophilic polymer used as a filler material can be either amphoteric (anionic and cationic monomers) or anionic or cationic, or non-ionic or Zwitterionic for both crosslinked beads or granules and uncrosslinked polymers. There are several effective forms for the crosslinked polymers. The hydrogel polymers can be crosslinked through covalent bonds, crystalline domains, ionic bridges or hydrophobic or hydrophilic associations. Examples of crosslinked polymers for the beads or granules are: poly(acrylamide), poly(N-vinyl-2-pyrrolidone), polyacrylates, poly(vinylalcohol), poly(ethylene oxide) and crosslinked polysaccharides. Superabsorbents such as sodium carboxymethyl cellulose and poly(acrylic acid) salts can also be used. Superabsorbents have been widely used in diapers and feminine hygiene products due to their superior water absorbing capability.

Because most hydrogel beads or granules used in the prosthetic disc have a water content of more than 70%, they are very flexible and compressible, although their tensile strength might not be very high. This flexibility and compressibility will assure that the particles will not be broken to smaller pieces under compressive and shear forces.

The hydrogel beads used in the disc of the present invention, as with many other hydrogels, can be dehydrated and then hydrated again without changing the properties of the hydrogel. When the hydrogel is dehydrated, its volume will decrease, which makes it possible to implant the prosthetic nucleus through a small window in the annulus or even possibly percutaneously.

When the particulate filler material is exposed to body fluid, it can spontaneously imbibe a large amount of water while still remaining an individual particle. The volume of the material will also increase significantly when the dry polymer starts to absorb water. Under the unconstrained conditions, the swelling of the polymer will reach an equilibrium. It would be more desirable to have the equilibrium volume of the hydrogel larger than the cavity in the disc. In this case, the swelling of the implant will be stopped as the swelling pressure is balanced with the external pressure, and consequently there will always be a driving force for the hydrogel to absorb more water if the external pressure is reduced or removed. This is a situation very similar to the natural nucleus, which is always constrained by the annulus and endplates.

Because the volume of the implant is very small, when the semi-permeable membrane with the particulate hydrogel filler is in the dry form it can be folded and implanted through a very small window on the annulus either in open surgery or percutaneously after the degenerated nucleus has been removed. Because higher water content hydrogels can be used in the present invention, the volume of the implant with dry polymers inside would be smaller than that of the dry bulk hydrogel prosthetic disc. When either prosthetic disc is implanted, they will quickly absorb water from bodily fluids and inflate. The size increase will prevent the implant from being extruded back out through the annulus wall. The expanded implant will conform to the disc nucleus space because of the flexibility of the membrane. Eventually, the swelling pressure of the device will be balance with the external constraining pressure from the annulus and the endplates. When the load increases as the patient lifts weight or bends at a certain angle, the established equilibrium is disturbed, i.e. the external pressure is greater than the swelling pressure. This stress imbalance causes fluid to be expressed from the hydrogel through the semi-permeable membrane. As fluid is expressed, the swelling pressure rises to achieve a new balance. In the same way, when the load is released, the implant will absorb more fluid and the disc space will be restored.

These and other objects of the present invention are disclosed in a preferred embodiment of the invention which includes a prosthetic nucleus for a disc which is composed of a hydrogel material. The bulk hydrogel prosthetic nucleus, as inflated, has a shape and size generally conforming to the natural nucleus which has been removed in a regular discectomy procedure and has a water content of at least 30%, preferably 70–85%, with a compressive strength of at least 4 Meganewton per square meter ($MNm^{-2}$) or greater when hydrated to its equilibrium water content. While the preferred bulk nucleus may have a water content of 70% to 85% when fully hydrated, it may have a water content of up to 90%.

After hydration in the disc, the bulk hydrogel nucleus will be constrained tightly in the cavity from which the nucleus has been excised. The constraining forces are the restoring force of the stretched fibers of the annulus and the external force through the end-plates. The constraint from the annulus and the end-plates will restrict the movement of the hydrogel nucleus and prevent it from bulging and herniating from the cavity.

The bulk prosthetic nucleus may be formed from two or more pieces of hydrogel material, each shaped so that when combined they have a shape generally conforming to the natural nucleus. Utilizing a two-piece prosthetic nucleus facilitates implantation, which is done with the hydrogel material in a dehydrated or unhydrated state.

The prosthetic nucleus made of the particulate hydrogel with the membrane cover of the present invention has a water content of between 30% to 99%, preferably 75% to 95% when hydrated within the disc. The volume of the cover as the hydrogel hydrates expands to fill the cavity in the disc and again the shape will generally conform to the natural nucleus.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings wherein similar reference characters denote similar elements throughout the several views, in which.

DESCRIPTION OF THE PREFERRED EMBODIMENT

Figure 1:
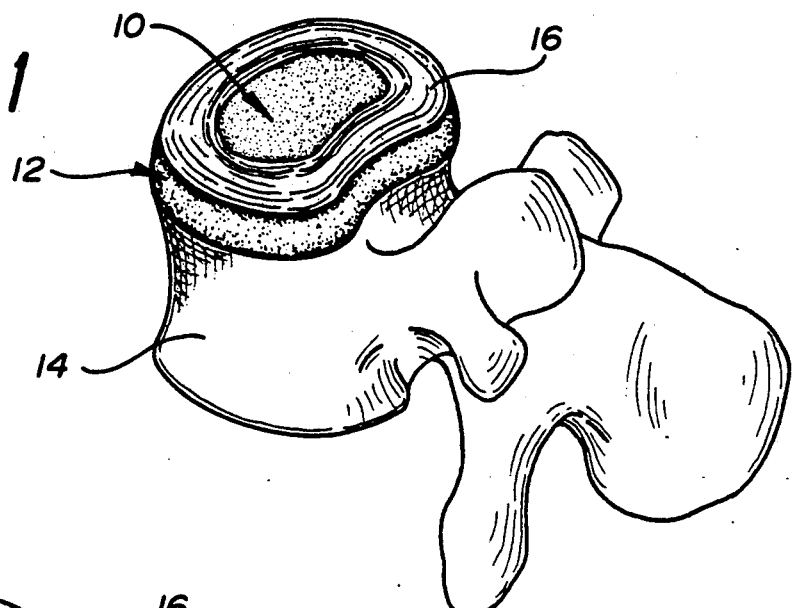
FIG. 1 is an isometric view of a single vertebral disc with the nucleus exposed.
Figure 2:
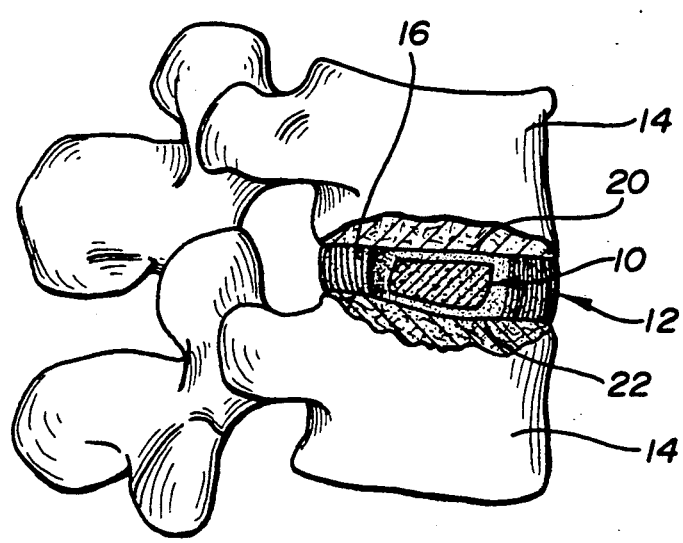
FIG. 2 is an elevation view, partially in cross-section, of a disc with the prosthetic nucleus of the present invention shown in the dehydrated state.
Figure 3:
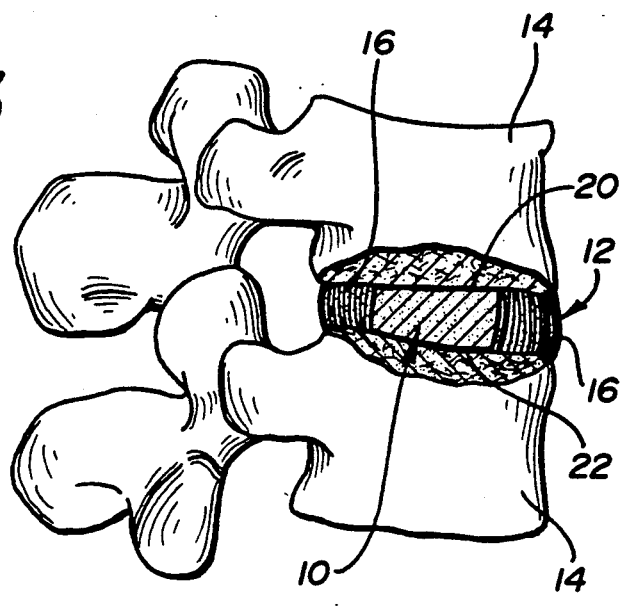
FIG. 3 is the disc of FIG. 2 showing the prosthetic nucleus of the present invention in the hydrated state.

Referring to FIGS. 1 through 9, in the preferred embodiment the prosthetic nucleus of the present invention generally denoted as 10 is shaped to conform, when hydrated, to the general shape of the natural nucleus. The nucleus is implanted in disc 12 of vertebrae 14 and is surrounded by the natural annulus fibrosus 16. Vertebral end plates 20 and 22 cover the superior and inferior faces of nucleus 10 respectively. The preferred material of nucleus 10 is a hydrogel material, preferably highly hydrolysed polyvinyl alcohol (PVA). The amount of hydrolization may be between 95 and 100 percent depending on the preferred final water content desired which is about 70% to 85%. Generally, the final hydrogel water content increases as the percent of hydrolization of the initial PVA decreases.

EXAMPLE

The general technique of preparing PVA bulk hydrogel from the commercially available PVA powder has been disclosed in the U.S. Pat. No. 4,663,358, the teachings of which are incorporated herein by reference.

Typically, 10-25% PVA powder is mixed with a solvent, such as water, dimethyl sulfoxide, ethylene glycol or a mixture thereof. The slurry is then heated until a uniform gel is formed. The gel is then poured or injected into either a metal or a plastic mold which will give the shape and the size of the prosthetic nucleus. After cooling the gel below $-10°$ C. for crystallization for several hours, the shaped PVA gel will be soaked with water until all the organic solvent has been exchanged with water. The hydrated PVA gel can then be dehydrated for implantation. The PVA hydrogels thus prepared will have a water content between 60-90% and compressive strength greater than 4 $MNm^{-2}$. For a beaded hydrogel the beads are made from a 5 to 25% PVA powder using the same process as described above.

While PVA is used in the preferred prosthetic disc, other hydrogels such as lightly cross-linked polymers of 2-hydroxyethyl methacrylate, or copolymers and terpolymers made from the combination of the monomers of an N-vinyl monomer, (for example, N-vinyl-2-pyrrolidone (N-VP)), a hydroxy alkyl methacrylate ester, (for example, 2-hydroxylethyl methacrylate (HEMA)), an alkyl methacrylate (for example, methyl methacrylate (MMA)), an ethylenically unsaturated acid (for example, methacrylic acid (MA)) and an ethylenically unsaturated base (for example, N,N-diethylamino ethyl methacrylate (DEAEMA)) may be used.

HYPAN TM (hydrogel polyacrylonitrile) is another type of hydrogel which can be used as a hydrogel nucleus. This hydrogel, unlike the cross-linked hydrogel, has a multi-block copolymer (MBC) structure with hard crystalline nitrile blocks which gives the hydrogel good mechanical properties and soft amorphous hydrophilic blocks which gives the hydrogel good water binding capability. The methods of preparing the HYPAN TM hydrogels of different water contents and different mechanical properties have been disclosed in the U.S. Pat. Nos. 4,337,327, 4,370,451, 4,331,783, 4,369,294, 4,420,589, 4,379,874 and 4,631,188. The device of this material can be either melt compressed as thermoplasts or injection molded.

In general, any hydrogel that can be used for soft contact lenses can be used as long as the hydrogel exhibits a compressive strength of at least 4 $MNm^{-2}$. Most of these materials have been FDA approved for use as contact lenses. Of course, many other hydrogel compositions may be used since, unlike contact lenses, opaque materials are acceptable. The art of preparing these polymers and copolymers has been disclosed in numerous U.S. patents. The water content of these hydrogels can vary from 38% for polymacon (poly HEMA) to 79% for lidofilcon B (copolymer of N-VP and MMA).

A prosthetic nucleus made from these hydrogels can be prepared either by cast molding or lathe cutting. In cast molding, the liquid monomer mixture with initiator is poured into a mold of the predetermined shape and size. It is then cured in the mold. In the case of lathe cutting, the polymer can be prepared in a similar manner in the form of a block or rod which is larger than the prosthetic nucleus. The polymer then will be cut to the shape and size of the nucleus. In both cases, the hydrogel expansion factor due to polymer swelling upon hydration has to be taken into account in designing the mold or in cutting the prosthetic nucleus.

Prosthetic nuclei 10 of various shapes can be designed as required to restore the function of the degenerated disc. In the preferred embodiment, the prosthetic nucleus approximates the shape and size of the natural nucleus, resembling an eclipse as shown in FIG. 1. The exact size of the hydrated prosthetic nucleus can be varied for different individuals. A typical size of adult nucleus is 2 cm in semi-minor axis and 4 cm in semi-major axis and 1.2 cm in thickness.

Figure 4:
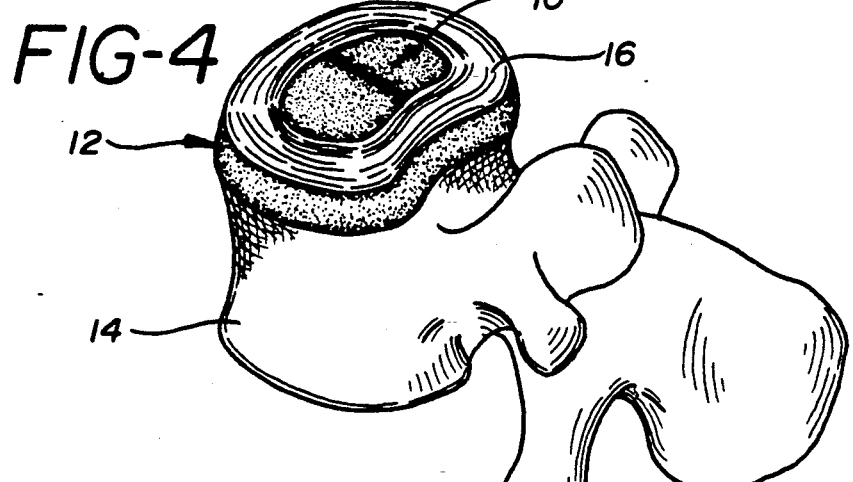
FIGS. 4 through 6 show three embodiments of a two-part prosthetic nucleus of the present invention in the hydrated state implanted within a vertebrae.
Figure 5:
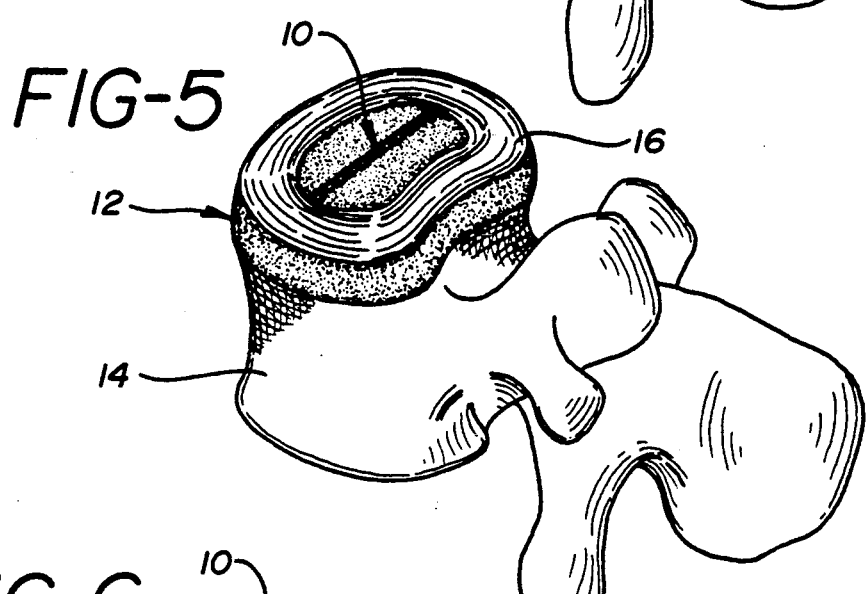
Figure 6:
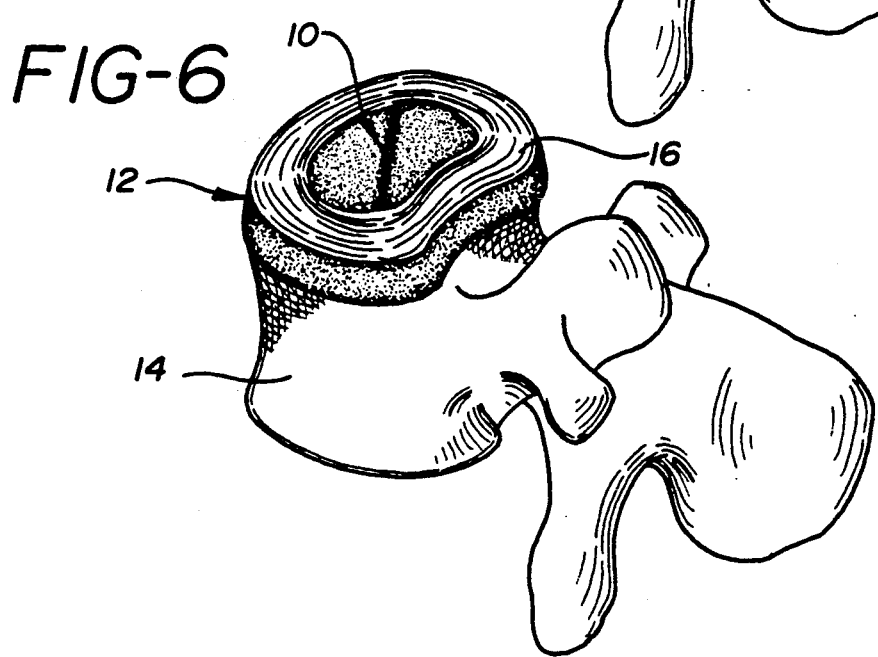
Figure 7:
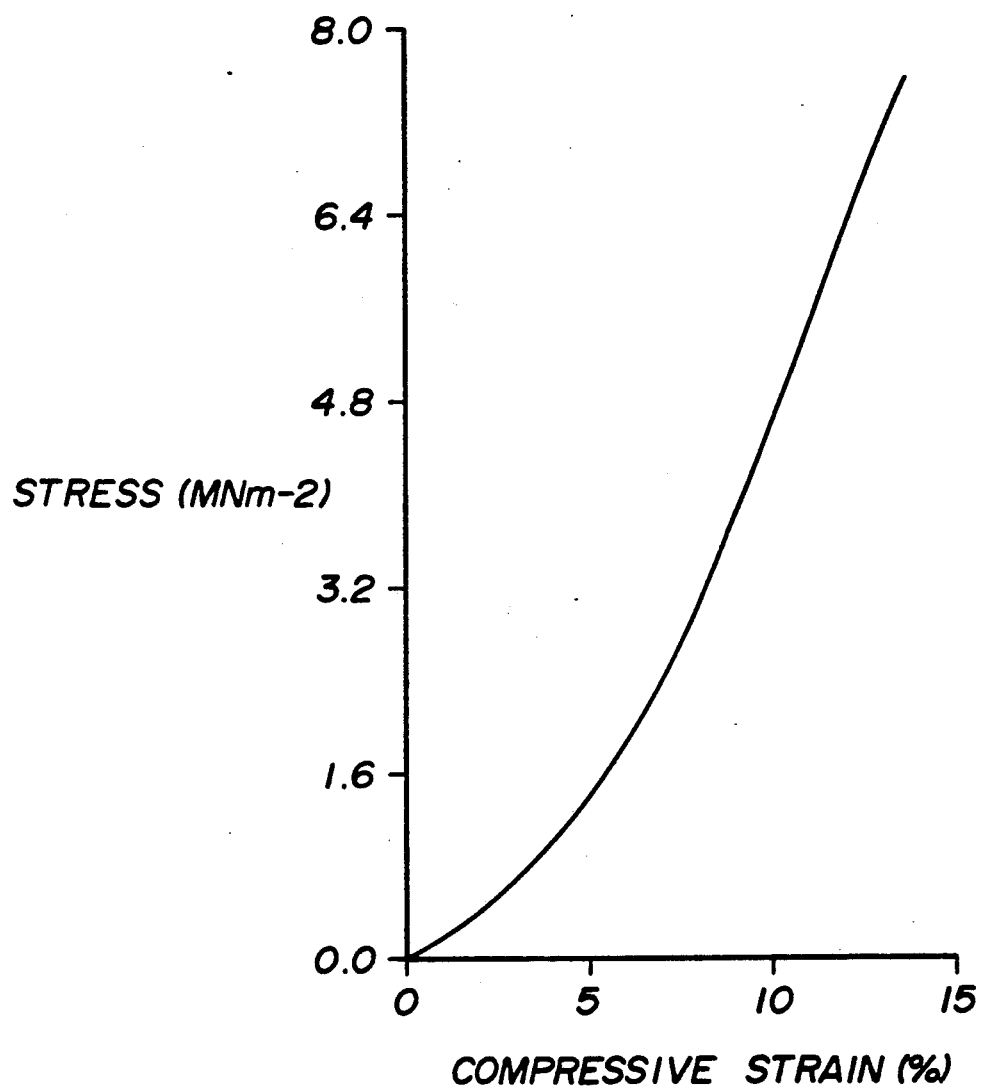
FIG. 7 is a graph showing the result of a stress vs strain test of a PVA hydrogel.

In an alternate embodiment shown in FIGS. 4-6, the prosthetic nucleus has two halves having the combined shape of a natural nucleus. Several designs of the two-part implants can be used. The first one of these is made by dividing the nucleus longitudinally (FIG. 4). The other is made by dividing the nucleus transversely (FIG. 5). Another design is to divide two halves laterally (FIG. 6). The major advantage of the two-part design is that the incision area can be further reduced and it is easier to manipulate the implants during surgery.

The surface of the implants can either be smooth or have transverse grooves (not shown) to increase the stability of the prosthesis in the disc cavity. To better fit into the vertebral body, the surface of the one piece prosthesis can be slightly convex because the surface of the vertebral body is slightly concave.

The shaped hydrogel of the present invention has a much higher structural integrity than the natural nucleus (shaped gel vs loose gel). This is because unlike the loose gel of the natural nucleus, the shaped gel has shape memory because the polymer matrix has cross-linking or strong hydrogen bonding. However, it will still have extensive lateral bulging under high compressive load if there is no boundary to constrain the deformation. Because use of the present invention does not involve any removal of the disc annulus and end-plates, the lateral bulging of the hydrogel nucleus will be restricted by the restoring force of the stretched fibers. Also, due to its superior structural integrity, the hydrogel nucleus will not herniate or bulge through the previously herniated areas or the incision which was made to remove the degenerated nucleus.

The stress vs strain curve of the PVA hydrogel of 74% water content made from 10-25% PVA powder as described above is presented in FIG. 7. To mimic the constrained environment in which the nucleus is contained, a 1.0" in diameter and 0.8" in height PVA hydrogel disc was constrained in a connected three-piece test fixture having two rigid metal sleeves on each side with a flexible Tygon tube with wall thickness of ⅛" in the middle. All three pieces have an inner diameter of 1". The PVA hydrogel was then compressed in between two 1" diameter solid cylinders inserted in either end of the test fixture and compressed in an Instron ® testing machine and the stress vs strain curve was recorded. This setup, under the test stress range, would allow the hydrogel to bulge about 1-2 mm laterally, which is close to the lateral bulging reported previously in human spinal disc tests (Reuber, M., et al, Journal of Biomechanical Engineering, volume 104, 1982, p. 187). Again, the extent of directional bulging of the prosthetic nucleus of the present invention would still be largely dependent on the restoring forces of the annulus. This stress vs strain curve of the PVA hydrogel demonstrated that the PVA hydrogel offers similar or superior load resistant characteristics to the intervertebral disc. A compressive load of up to 4000N was exerted on the hydrogel, indicating that the hydrogel is strong enough to withstand a load in excess of those normally generated by the body in various postures.

Figure 8:
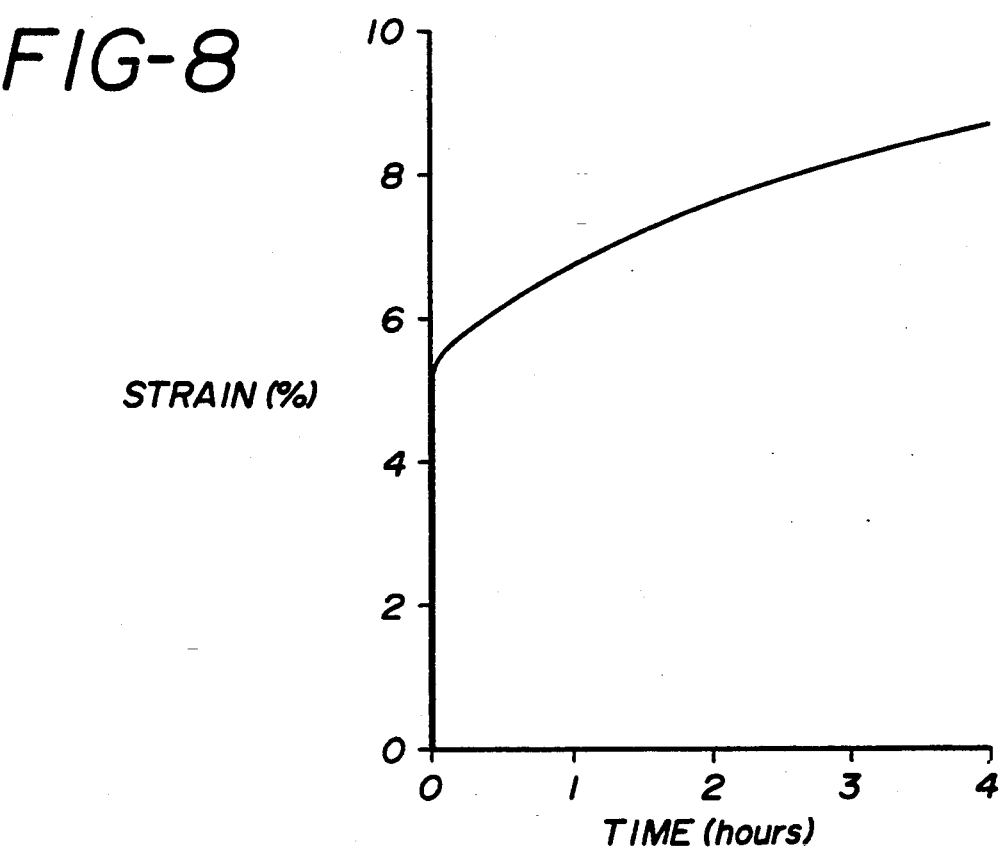
FIG. 8 is a graph showing the result of a creep test of a PVA hydrogel.
Figure 9:
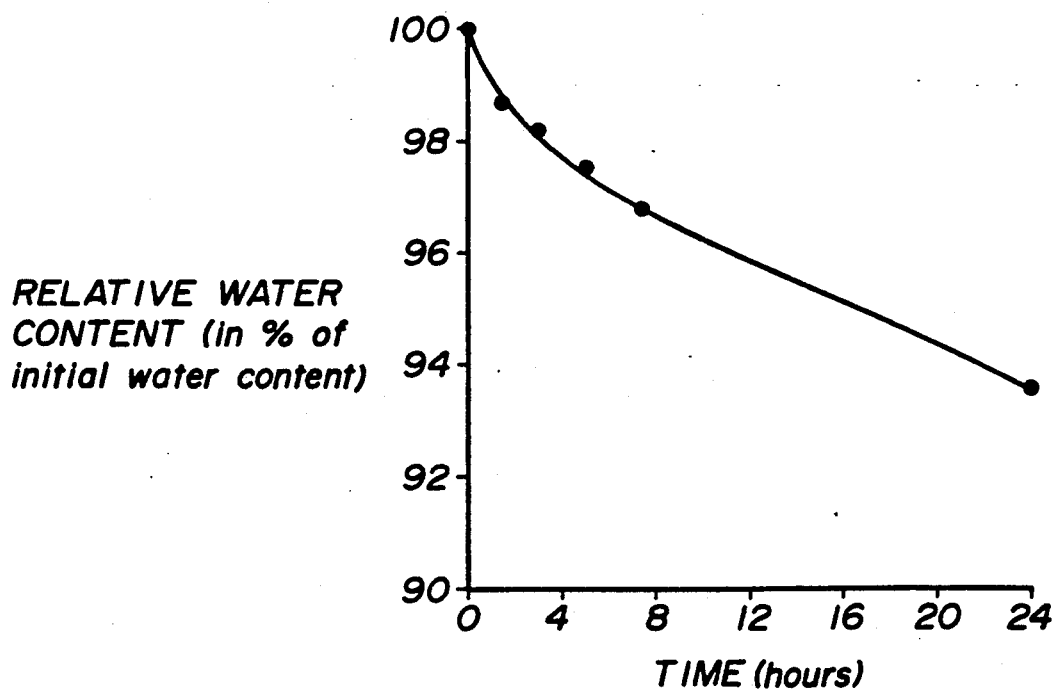
FIG. 9 is a graph showing the result of water content change vs time of a PVA hydrogel under constant compressive load.
Figure 10:
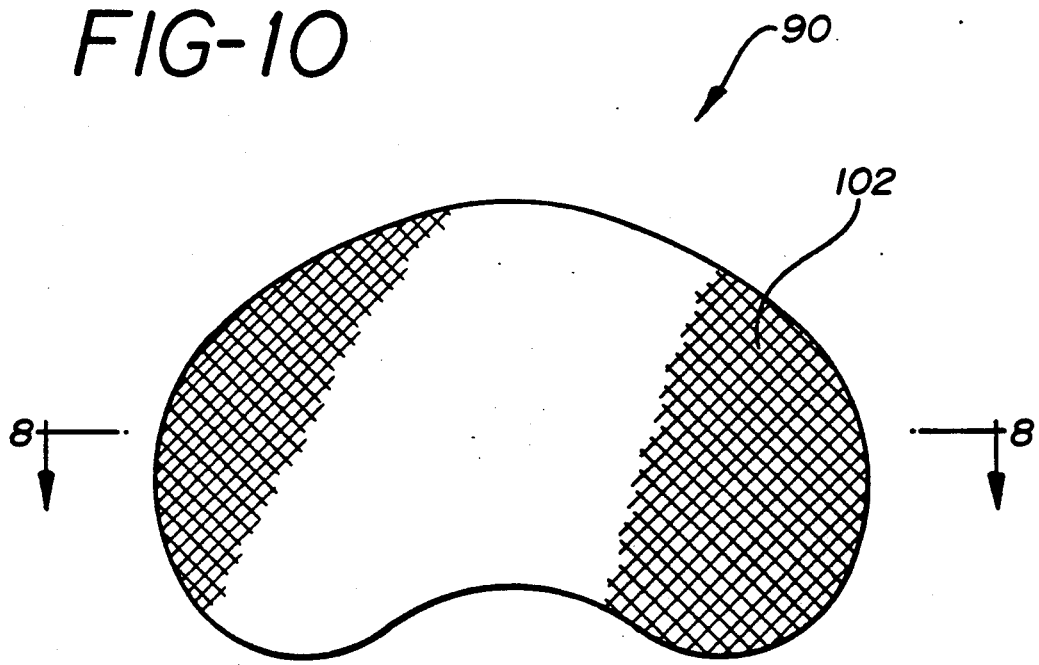
FIG. 10 is a plan view of a prosthetic nucleus having a membrane cover.
Figure 11:
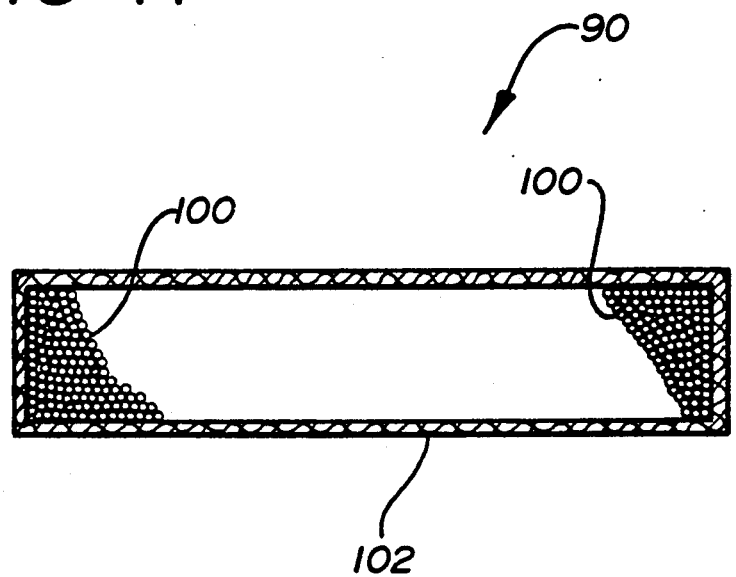
FIG. 11 is a cross-sectional view of the prosthetic nucleus of FIG. 10 along the lines 11—11 showing the cover of FIG. 10 enclosing a multiplicity of hydrogel beads.

Because the natural nucleus is also primarily a hydrogel, the implanted hydrogel artificial nucleus can easily restore all the biomechanical functions of the nucleus which has been removed. Unlike the prior art prosthetic discs, the hydrogel nucleus in the present invention will restore the visco-elastic behavior of the disc due to the water binding capability of the prosthetic hydrogel. FIG. 8 presents the creep behavior of the same PVA hydrogel of 74% water content. This hydrogel was tested in the same device as described above in the test of FIG. 7. The creep curve of the hydrogel is very similar to creep curve obtained in the human spinal disc reported elsewhere (Adam, M. A., and Hutton, W. C., The Biology of the Intervertebral Disc, Vol. II, 1988, p. 64). The initial, almost instantaneous, deformation in the disc arises mainly from a rearrangement of the collagen network in the annulus. The initial deformation in this case is mainly due to the stretching of the Tygon tube. If the load is maintained, the disc continues to deform or creep largely because the fluid in the nucleus is being squeezed out. This is shown in FIG. 9 in which the percentage of water relative to the initial water content was plotted vs time when constant load was applied. This visco-elastic characteristic, as mentioned above, is critical in withstanding the mechanical load and keeping the fluid flowing in and out of the disc.

Referring to FIGS. 10–18 yet another embodiment of the prosthetic nucleus of the present invention is disclosed. The prosthetic nucleus of this embodiment, generally denoted as 90, is shaped to conform, when hydrated, to the general shape of the natural nucleus. Again, the nucleus is implanted in disc 12 of vertebra 14 and is surrounded by the natural annulus fibrosus 16. Vertebral endplates 20 and 22 cover the superior and inferior faces of nucleus 90 respectively. The preferred material of nucleus 90 is a beaded or particulate hydrogel material 100, preferably highly hydrolized PVA. Hydrogel beads 100 are surrounded by a membrane 102 which may be made from nylon or dacron in woven form or may be made from various materials described below which produce the desired porosity.

Figure 12:
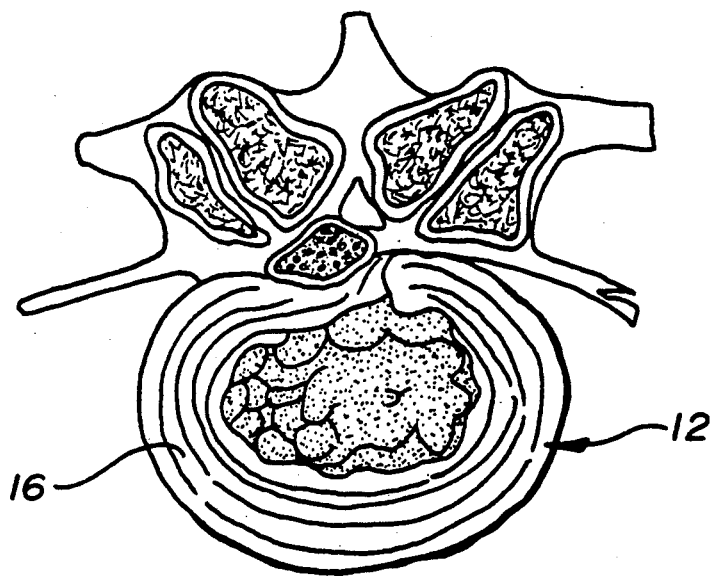
FIG. 12 is a cross-sectional view of a herniated vertebral disc.
Figure 13:
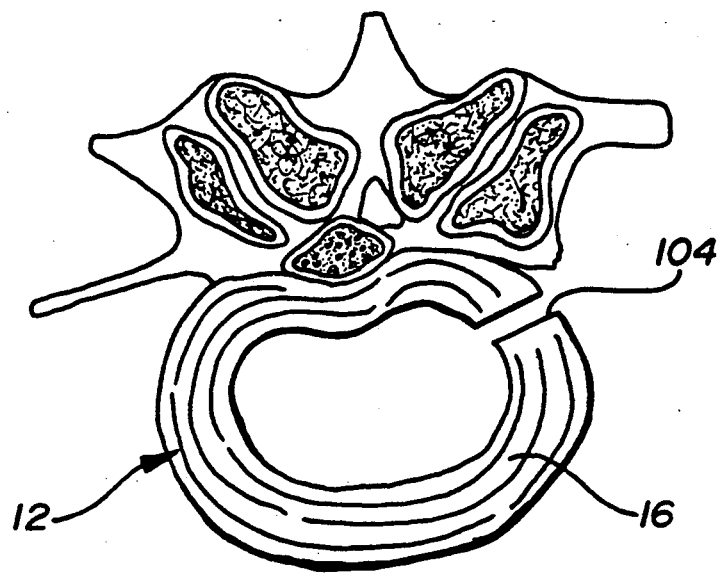
FIG. 13 is a plan view of the vertebral disc shown in FIG. 12 after the nucleus has been removed.
Figure 14:
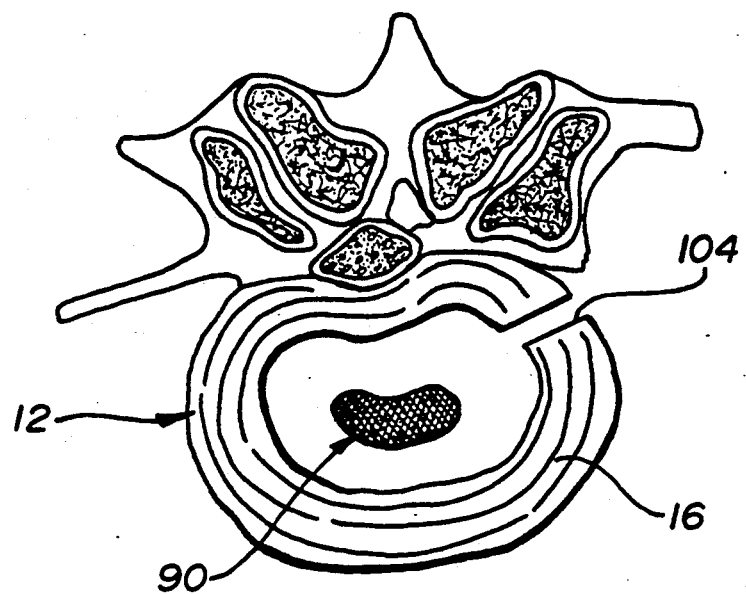
FIG. 14 is a plan view of the vertebral disc shown in FIG. 13 with the membrane covered prosthetic nucleus of the present invention implanted therein.
Figure 15:
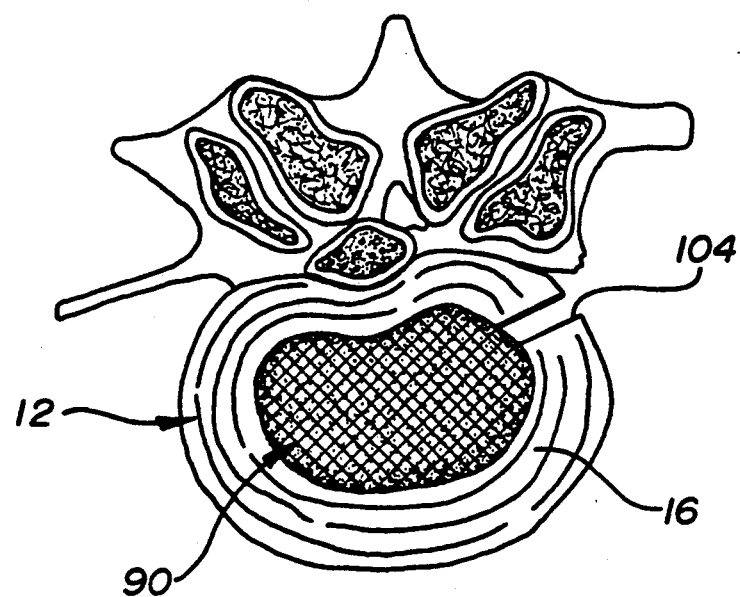
FIG. 15 is a plan view of the vertebral disc of FIG. 14 after the membrane covered prosthetic nucleus of the present invention has become hydrated.
Figure 16:
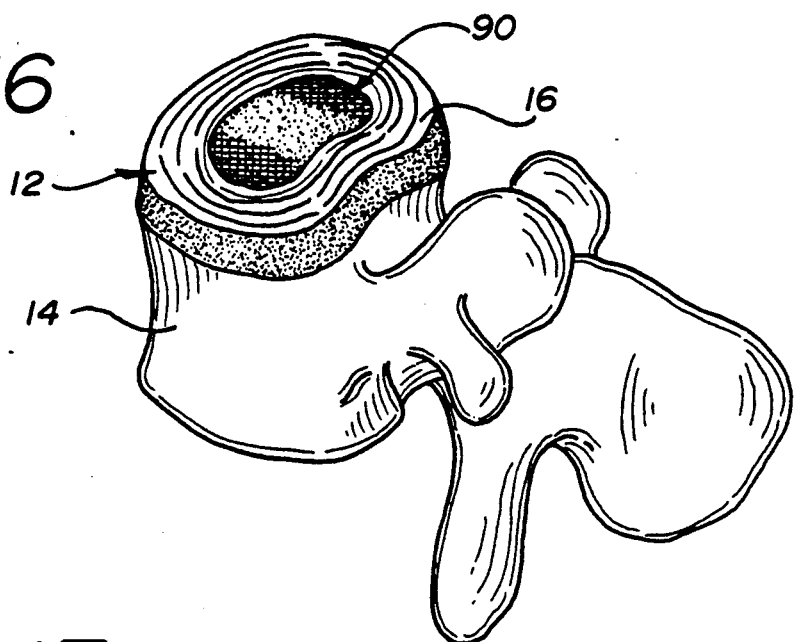
FIG. 16 is an isometric view of the vertebral disc of FIG. 15.
Figure 17:
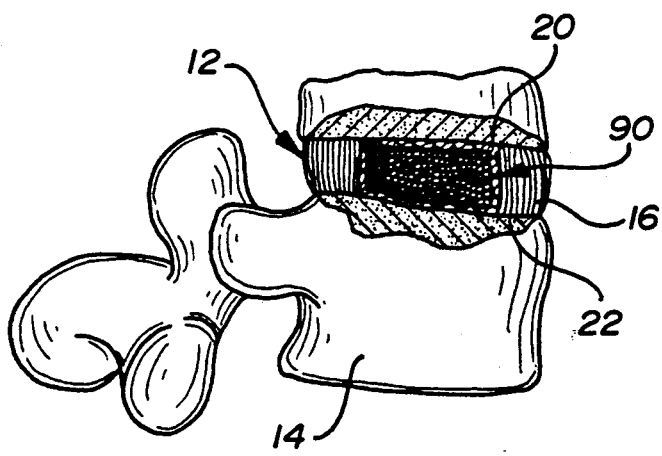
FIG. 17 is a partial cross-sectional view of the prosthetic nucleus shown in FIG. 16.
Figure 18:
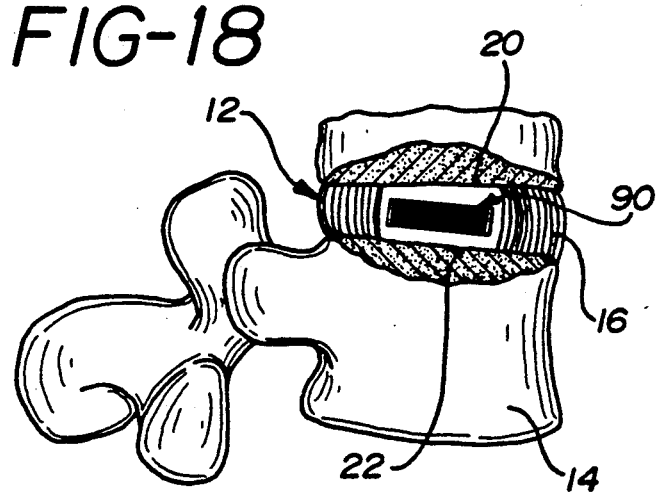
FIG. 18 shows the prosthetic nucleus of FIG. 17 prior to being hydrated.

In using prosthetic nucleus 90, the natural nucleus of a herniated disc as shown in FIG. 12 is removed via an opening 104. The prosthetic nucleus 90 is then inserted through opening 104 in its dehydrated state as shown in FIG. 14. FIG. 15 then shows the prosthetic nucleus 90 hydrated sufficiently to fill the cavity vacated by the natural nucleus. Since the membrane gives the prosthetic nucleus its mechanical strength, there is no possibility that the hydrogel material can leak out through opening 104. FIGS. 16–18 again show prosthetic nucleus 90 implanted within a vertebral disc.

The implantation of prosthetic nucleus 10 or 90 can be performed in conjunction with a laminectomy operation, such as discectomy or microdiscectomy, percutaneous discectomy, or chemonuclealysis. Because the properties of the hydrogel prosthetic nucleus of the present invention are similar to those of the nucleus material, the herniated nucleus can be partially or totally replaced by the hydrogel prosthetic nucleus. Due to its small size, a posterior lateral approach can be used to implant the dehydrated hydrogel disc. This significantly reduces the difficulty and the risk of the operation.

The volume of a hydrogel nucleus of 80% water content will reduce by about 80% (to 20% of its original volume) when dehydrated. Consequently, the surgeon does not need to jack apart the vertebrae adjacent to a damaged disc as required by, for example, the device disclosed in U.S. Pat. No. 4,772,287. The height of the dehydrated prosthetic nucleus, when inserted, is smaller than the disc space. Furthermore, the rigidity of the dehydrated prosthetic nucleus will help the surgeons to manipulate the prosthetic nucleus during the operation. After implantation, the hydrogel nucleus of the present invention swells slowly in the body to a predetermined height which is enough to maintain the space between the vertebral body. The swelling process normally takes several hours to two days depending on the size of the prosthetic nucleus and type of hydrogel.

The alternate prosthetic nucleus of the present invention using a beaded hydrogel shown in FIGS. 9 to 18 uses a high strength, but flexible, polymer membrane outer cover 102 shaped like the natural nucleus as it is inflated with hydrogel beads in the disc. This membrane can also be used to cover the bulk hydrogel if desired. Because the membrane used is flexible, the shape of the inflated outer shell does not need to be exactly the same as the cavity in the disc. As long as the volume of inflated membrane cover 102 is slightly larger than the cavity and the shape of the shell is not too different from that of the cavity, the final shape and size of the prosthetic nucleus will conform with the size and shape of the cavity created in the discectomy procedure. The functions of the membrane outer shell in the prosthetic nucleus are to provide the mechanical strength and general shape for the prosthetic nucleus and to block unwanted substances from penetrating into the prosthetic nucleus. To avoid the excess tensile strength that the swelling hydrogel will apply on the membrane, it is always more desirable to make the volume of the membrane outer shell slightly larger than the cavity in the disc. In this way, the membrane will be back-supported by the annulus and the endplates.

The membrane used for this purpose can be chosen from many commercially available materials including ultra high molecular weight polyethylene, poly(ethylene terephthalate), polytetrafluoro ethylene polyester, nylon and polysufone. The structure of the membrane outer cover can either be woven or nonwoven or may be braided, as long as the membrane is strong enough to withstand the pressure applied.

The porosity of membrane 102 can be controlled by the size of fiber and fiber density of the membrane, which varies with the technique used to fabricate the membrane. A single layer membrane can be used if the porosity of that single layer membrane is small enough for the purpose. If smaller porosity is required, a double layer or multi-layer membrane can be used. In a typical double layer membrane, there is a high strength polymer layer with large porosity for the backing, mainly to provide the mechanical strength of the membrane, and a layer which is somewhat weak but has the required porosity attaching to the backing layer. If the weak membrane layer does not have good wearing resistance, a multi-layer membrane can be used in which the weak membrane with the required porosity is sandwiched in-between the two strong backing layers of the same or different materials.

The porosity of the membrane has to be significantly smaller, preferably three times smaller than the smallest beads or particles used. The reason for this requirement is obvious since one does not want the filler materials (beads or granules) to be extruded out of the membrane. For most commercially available hydrogel beads or granules, the particle size is normally listed and can be well controlled. For example, the particle size of Sephadex ® beads available from Pharmacia is listed as 40-120 μm. In this case it is safe to have the membrane pore size less than 10 μm. (If the hydrogel used has an adverse reaction with or is rejected by some human cells, it is also preferable to have the membrane porosity less than the smallest cells in the human body. Smaller cells in the human body are red blood cells, which have the diameter of about 7 μm. To meet this requirement, the membrane must have a pore size of less than 7 μm, preferably less than 1 μm.)

Furthermore, some filler hydrogel particulate materials will be degraded by certain enzymes in the body. To prevent enzymatical degradation, it is preferable to have a membrane porosity of less than the dimension of the enzymes. For most enzymatic materials the molecular weight is above 15,000 daltons, which has the dimension of approximately 25 Å, depending on the shape of the enzyme. Therefore, an ultrafiltration membrane is needed. The porosity of this membrane should have the molecular weight cut-off (MWCO) of 15,000 daltons or less (to achieve porosity at this level on the woven membrane becomes unlikely). The materials used to make this membrane can be cellulose, cellulose ester, a mixture of cellulose ester and cellulose nitrate, and their derivatives. Such a membrane may be purchased from Spectrum Medical Industries. Because the mechanical strength of these ultrafiltration membranes is not as strong as woven membranes, a double layer or multiple layer woven outer cover is necessary for the prosthetic nucleus with an ultrafiltration membrane for the inner layer of the cover or sandwiched between two strong polymer layers.

If the ultrafiltration membrane is used, the filler material can also be uncrosslinked hydrophilic high molecular weight polymers, such as polysaccharide. The molecular weight of the filler material must be larger than the molecular weight cut-off of the membrane. Without the ultrafiltration membrane, as disclosed in U.S. Pat. No. 4,904,260 (Ray et al), the molecules in the solution will be leached out or degraded by enzymatic materials.

An example of a double layer membrane is available from Gelman Sciences (MI). Both hydrophobic and hydrophilic membranes with various pore size (0.1 μm-10 μm) are available. Generally, a hydrophobic membrane such as Versapel ® can be made to be hydrophilic by coating with a wetting agent (then sold as Versapor ®). The membrane is manufactured with a non-woven polymer (nylon or polyester) for backing with various coated microporous polymer films (urethane/fluoropolymer, acrylic copolymer or polysulfone) by a UV/E-Beam polymerization process. The following table summarizes the data of these membranes.

| Trade/ Reg. Name | High Strength Backing Polymer | Microporous Polymer | Hydrophilic/ Hydrophobic | Pore Size Available |
|---|---|---|---|---|
| Repel ™ | Polyester | Urethane/ Fluoropolymer | Hydrophobic | 0.1, 0.2 μm |
| Versapel ® | Nylon | Acrylic Copolymer | Hydrophobic | 0.2-10 μm |
| Versapor ® | Nylon | Acrylic Copolymer | Hydrophilic | 0.2-10 μm |
| Thermapor ™ | Polyester | Polysulfone | Hydrophilic | 0.45, 0.8, 3 μm |

These membranes have been proved to be chemically inert and biologically safe. The membrane can be sterilized by using autoclave, gamma radiation or ethylene oxide methods. They are also compatible with heat, radio frequency and ultrasonic sealing methods.

The dimension of the membrane capsule when inflated should be about the same as or slightly bigger than the size of the cavity in the disc created from the discectomy. The size of the cavity in the disc is dependent on the size of the disc, the degree of degeneration and the level of the disc. Typically, it varies from 2 cm$^3$ to 7 cm$^3$.

To increase biocompatibility and decrease friction between the membrane and the surrounding tissues, the membrane can be coated with a material which can enhance these features. The examples of this coating material are hyaluronic acid (HA), polyvinyl alcohol (PVA), polyethylene glycol and polyurethane which are all considered biocompatible and low friction.

Coating techniques may be used to decrease the friction of the outer cover surface and to increase the biocompatibility and include graft polymerization, plasma polymerization, chemical vapor deposition and photolithographic processes. In addition, it is not necessary for the entire surface to be permeable. Because it is an enclosed device, there has to be an opening for introducing the filler of dry beads or particles, into the device before the prosthetic nucleus can be sealed. The techniques of sealing the opening in the fabric cover are well known and include heating, radio frequency, and ultrasonic sealing or using adhesive agents with these techniques.

The prosthetic nucleus capsule can be sealed with dry hydrogel beads inside before implantation. An alternative is to insert the empty membrane outer cover which is attached to a tube between the hydrogel filler into the capsule. After insertion, the dry hydrogel beads or semi-dry hydrogel beads are injected into the membrane cover through the tube. The end of the tube is then sealed simply by heating method and inserted into the cavity. Again, nonpermeable material can be used for the tube attached to the membrane cover.

The permeability of the natural endplates, through which most bodily fluids diffuse in and out of the disc, has been reported to be in the order of $10^{-17} m^4 N^{-1} sec^{-1}$. This number is smaller than the permeability of most membranes. Therefore, the natural creep rate and the other natural biomechanical properties would not change significantly as the nucleus is replaced by the prosthetic implant of the present invention.

As noted, hydrogels have also been used in drug delivery due to their capability for a controllable release of the drug. Different therapeutic agents, such as different growth factors, long term analgesics and anti-inflammatory agents can be attached to the prosthetic nucleus and be released in a controllable rate after implantation.

While several examples of the present invention have been described, it is obvious that many changes and modifications may be made thereunto, without departing from the spirit and scope of the invention.

We claim:

1. A prosthetic nucleus for implanting in the disc space after the removal of the degenerated or damaged nucleus of an intervertebral disc comprising:

A multiplicity of hydrogel beads having a water content of at least 30%; and a flexible semi-permeable cover surrounding said hydrogel beads.

2. The prosthetic nucleus as set forth in claim 1 wherein said hydrated hydrogel beads each have a water content of between 75 and 99%.

3. The prosthetic nucleus as set forth in claim 1 wherein each hydrogel bead when dehydrated has a volume of 2–70% of a hydrated hydrogel bead.

4. The prosthetic nucleus as set forth in claim 1 wherein said hydrated hydrogel beads each have a particle size of at least three times larger than the porosity of the membrane.

5. The prosthetic nucleus as set forth in claim 1 wherein the hydrogel beads are made from crosslinked polysaccharide.

6. The prosthetic nucleus as set forth in claim 1 wherein the hydrogel beads are made from a 5–25% PVA powder mixed with a solvent selected from the group consisting of water, dimethyl sulfoxide, ethylene glycol and a combination thereof.

7. The prosthetic nucleus as set forth in claim 6 wherein the hydrogel beads are prepared by crystallizing a solution of polyvinyl alcohol at a temperature of −10° C. or below.

8. The prosthetic nucleus as set forth in claim 1 wherein the hydrogel beads are prepared by the polymerization of monomers selected from the group consisting of: N-vinyl monomer (e.g. N-vinyl-2-pyrrolidone), hydroxy alkyl methacrylate (e.g. 2-hydroxylethyl methacrylate), alkyl methacrylate (e.g. methyl methacrylate), ethylenical unsaturated and or its salt (e.g. methacrylic acid), ethylenically unsaturated base or its salt (e.g. N,N-diethyl-aminoethyl methacrylate and a combination thereof with a cross-linking monomer containing at least two ethylinic sites (e.g. ethylene glycol dimethacrylate).

9. The prosthetic nucleus as set forth in claim 1 wherein the hydrogel beads are made of polyacrylonitrile hydrogel.

10. The prosthetic nucleus as set forth in claim 1 wherein the hydrogel beads are superabsorbents such as sodium carboxymethyl cellulose and poly(acrylic acid) salts.

11. The prosthetic nucleus as set forth in claim 1 wherein the flexible semi-permeable membrane is made of a material selected from the group of polyester, polyolefine and poly(ethylene terephthalate), polytetrafluoro ethylene, polysulfone or nylon.

12. The prosthetic nucleus as set forth in claim 1 wherein the membrane structure is woven.

13. The prosthetic nucleus as set forth in claim 1 wherein the membrane has two layers with one layer providing the mechanical strength and another layer providing the necessary porosity for the membrane.

14. The prosthetic nucleus membrane as set forth in claim 13 wherein the membrane is made of a layer of nonwoven nylon for mechanical strength coated with a layer of microporous acrylic copolymer film.

15. The prosthetic nucleus membrane as set forth in claim 13 wherein the membrane is made of a layer of nonwoven polyester for mechanical strength coated with a layer of microporous urethane/fluoropolymer film.

16. The prosthetic nucleus membrane as set forth in claim 13 wherein the membrane is made of a layer of nonwoven nylon for mechanical strength coated with a layer of microporous acrylic copolymer film and a wetting agent.

17. The prosthetic nucleus membrane as set forth in claim 13 wherein the membrane is made of a layer of nonwoven polyester for mechanical strength coated with a layer of microporous polysulfone film.

18. The prosthetic nucleus as set forth in claim 1 wherein the membrane has multiple layers with a microporous layer being sandwiched in-between the two strong backing layers.

19. The prosthetic nucleus membrane as set forth in claim 18 wherein the microporous layer is an ultrafiltration membrane which is made of a member selected from the group consisting of cellulose, cellulose ester or a mixture of cellulose ester, cellulose nitrate and a combination thereof.

20. The prosthetic nucleus as set forth in claim 1 wherein the porosity of the semi-permeable membrane is at least three times smaller than the smallest particle size of the hydrated hydrogel beads.

21. The prosthetic nucleus as set forth in claim 1 wherein the porosity of the semi-permeable membrane is less than 7 μm.

22. The prosthetic nucleus as set forth in claim 1 wherein the porosity of the semi-permeable membrane has a molecular weight cut-off of 15,000 daltons.

23. The prosthetic nucleus as set forth in claim 1 wherein the surface of the membrane is treated.

24. The prosthetic nucleus membrane as set forth in claim 23 wherein the membrane is coated with a member selected from the group consisting of hyaluronic acid (HA), polyvinyl alcohol, polyethylene glycol, or polyurethane and a combination thereof.

25. The prosthetic nucleus membrane as set forth in claim 23 wherein the membrane is coated by a method selected from the group consisting of graft polymerization, plasma polymerization, chemical vapor deposition, photolithographic process and a combination thereof.

26. A prosthetic nucleus for implanting in the disc space after the removal of the degenerated or damaged nucleus of an intervertebral disc comprising:
a hydrogel material having, when hydrated in the disc, a water content of at least 30%; and
a semi-permeable membrane surrounding said hydrogel, and, when inflated, having a size and shape generally conforming to a natural nucleus.

* * * * *